United States Patent
Van Duren et al.

[11] Patent Number: 6,126,681
[45] Date of Patent: Oct. 3, 2000

[54] DETECTION OF A CONDITION BETWEEN AN INFLATABLE THERMAL DEVICE AND AN AIR HOSE IN A CONVECTIVE WARMING SYSTEM

[75] Inventors: Albert Philip Van Duren, Chaska; Allen Hamid Ziaimehr, Arden Hills; John Paul Rock, Minneapolis; Scott Douglas Augustine, Bloomington; Gary Rabindranath Maharaj, Eden Prairie, all of Minn.

[73] Assignee: Augustine Medical, Inc., Eden Prairie, Minn.

[21] Appl. No.: 09/138,774

[22] Filed: Aug. 24, 1998

[51] Int. Cl.[7] .............................. A61F 7/00; A61F 7/12; A61B 18/04; A61H 1/02; A61H 5/00
[52] U.S. Cl. .............................. 607/96; 607/98; 606/27; 601/16
[58] Field of Search .................. 601/148, 6, 16, 601/43; 128/200.24, 202.22; 607/98, 96; 606/27; 600/533, 532

[56] References Cited

U.S. PATENT DOCUMENTS

| | | | |
|---|---|---|---|
| 4,302,640 | 11/1981 | Vicenzi et al. | 200/81 |
| 4,316,182 | 2/1982 | Hodgson | 340/606 |
| 5,057,822 | 10/1991 | Hoffman | 340/611 |
| 5,300,098 | 4/1994 | Philipot | 607/96 |
| 5,300,101 | 4/1994 | Augustine et al. | 607/107 |
| 5,300,102 | 4/1994 | Augustine et al. | 607/107 |
| 5,320,092 | 6/1994 | Ryder | 128/202.22 |
| 5,324,320 | 6/1994 | Augustine et al. | 607/107 |
| 5,405,371 | 4/1995 | Augustine et al. | 607/107 |
| 5,626,129 | 5/1997 | Klimm et al. | 128/202.22 |
| 5,706,801 | 1/1998 | Remes et al. | 128/202.26 |
| 5,785,723 | 7/1998 | Beran et al. | 55/267 |
| 5,865,171 | 2/1999 | Cinquin | 128/203.12 |
| 5,881,717 | 3/1999 | Isaza | 128/202.22 |
| 5,950,621 | 9/1999 | Klockseth et al. | 128/204.26 |

FOREIGN PATENT DOCUMENTS

08322959  12/1996  Japan.

*Primary Examiner*—Linda G. M. Dvorak
*Assistant Examiner*—Jocelyn Debra Ram
*Attorney, Agent, or Firm*—Gray Cary Ware Freidenrich

[57] ABSTRACT

A condition is detected between an inlet port of an inflatable thermal device, such as an inflatable thermal blanket, and an end of an air hose through which a flow of pressurized, thermally treated air is provided to the device by way of the inlet port. The condition may be disconnection of the end of the air hose from the inlet port or a change in the value of an air flow characteristic such as temperature or velocity. A response to the condition may include provision of a perceptible indication that the condition has occurred. Other responses may include cessation of the flow of air or changing an air flow characteristic.

70 Claims, 11 Drawing Sheets

DETECTION OF A CONDITION BETWEEN AN INFLATABLE THERMAL DEVICE AND AN AIR HOSE IN A CONVECTIVE WARMING SYSTEM

BACKGROUND OF THE INVENTION

This invention relates to inflatable thermal devices that regulate human core temperature by convecting pressurized, thermally regulated air. More particularly, the invention relates to inflatable thermal blankets and the like that are used, for example, in a medical setting to deliver a bath of pressurized, thermally-regulated (heated or cooled) air for the treatment of hypothermia or hyperthermia. In particular, pressurized, thermally regulated air is used to inflate such a device and is expelled therefrom onto a person. Still more particularly, the invention relates to monitoring the operation of an inflatable thermal device in order to detect and respond to a potentially hazardous condition of its operation.

The International Electrotechnical Commission has promulgated a new standard (IEC 601-2-35) entitled Particular requirements for safety of blankets, pads and mattresses, intended for heating in medical use. This standard imposes requirements on the design and operation of convective warming systems. In particular, clause 46.101 states: "If omission of a part, or the interchange of parts of a multi-part heating device, will cause a safety hazard, the heating device shall be designed such that heat will be supplied only if all parts of the heating device are correctly positioned." This requirement is intended to prevent human error leading to patient injury.

In convective warming systems, an inflatable thermal device is used to deliver a bath of pressurized, thermally-regulated air to a person, animal, or thing. The device is inflated with the pressurized, thermally-regulated air and has one or more surfaces adapted for expelling the air onto a person. Such devices may lie on a person, around a person, or under a person. U.S. Pat. Nos. 5,324,320 and 5,405,371, for example, describe inflatable thermal blankets that lie on a person, expelling pressurized, warmed air through a lower surface that faces the person. U.S. Pat. No. 5,300,101 describes another inflatable thermal device that lies around the sides and at least one end of a person. Other kinds of inflatable thermal devices are contemplated, including those lying under a person. Therefore, when used, the term "inflatable thermal device" is intended to invoke any and all blankets, pads, mattresses, covers, and equivalent structures that operate as just described.

Typically, the inflatable thermal devices of interest convect pressurized, warmed air in response to a pressurized flow of warm air that is provided, for example, from a heater/blower unit through an air hose. Typically the inflatable device includes one or more inlet ports that receive one end of the air hose. The other end of the air hose is received in the heater/blower unit. When the heater/blower unit is turned on, air is warmed in the unit and pumped from the unit through the air hose to inflate the inflatable thermal device, whence the air is exhausted to warm a person. Such devices may exhaust the air through a plurality of punched holes, through porous material, or through air permeable material.

One hazard in convective warming systems that use inflatable devices is the risk of overheating or burning a person. In the first instance, air flow temperature may exceed a level necessary for proper treatment. In the second instance, the end of the air hose that is received in an inlet port may become dislodged and repositioned in such a way as to direct the pressurized, heated air flow directly onto a person. It is these hazards that are contemplated by the IEC standard. To date, means for detecting and mitigating these hazards have not been incorporated into the convective warming systems described above. Furthermore, in addition to the hazards contemplated by the new IEC standard, there is an operating deficiency common to many commercially available convective warming systems. This deficiency lies in the dependence of the air flow temperature at the distal end of an air hose on several environmental conditions which prevent accurate estimation of air hose outlet temperature.

The commercially available heater/blower units for convective warming systems include a heater and a blower which operate to provide a steady stream of temperature-conditioned air at a given mass flow. The temperature of the heated air ducted from the heater/blower unit through an air hose is tightly controlled at the heater/blower unit end of the air hose; however, the temperature of air flow introduced into the inflatable thermal device is a function of several factors, including, but not limited to: 1.) the capacity of the unit; 2.) the blower capacity; 3.) the length, thermal conductivity, and thermal emissivity of the air hose between the unit and the device; 4.) the fluid flow resistance of the device; and, 5.) the ambient conditions, of which temperature and external air velocity are the most important.

The exhaust (output) temperature of the flow of air leaving a heater/blower unit is generally tightly controlled by a unit temperature controller. The temperature controller continually senses the output temperature at a port in the unit where the proximal (near) end of the air hose is received and adjusts the heater unit power to maintain the output temperature at constant setting. The temperature of the air flow at the distal (far) end of the air hose (that is, the inlet temperature to the inflatable thermal device), however, depends greatly on the conditions listed above.

None of the commercially-available heater/blower units senses the air flow temperature at the inlet port, which can result in uncertain and poorly controlled delivery of therapy. When the air is being heated, the air flow temperature at the distal end of the air hose may actually rise (or fall) to a level which deviates from a desired target temperature at this point.

Accordingly there is a need to: 1.) prevent heater/blower unit misuse when the inflatable thermal device has been disconnected from the air hose; 2.) provide better control of air flow temperature at the distal end of the air hose irrespective of ambient conditions, resistive load of the inflatable thermal device, or heater/blower unit capability; and 3.) meet the requirements of the IEC standard.

SUMMARY OF THE INVENTION

The invention is based on the critical realization that the junction between the distal (far) end of an air hose and an inlet port of an inflatable thermal device provides a location where the continuity of the air flow path and the magnitudes of air flow characteristics such as temperature and pressure can be sensed. In this regard, a first circuit element may be provided that is integral with the inflatable thermal device at, in, or near an inlet port, while a second circuit element may be provided at, in, or on the distal end of the air hose. When the distal end of the air hose is received in the inlet port, the first and second circuit elements cooperate to provide a signal indicative of connection between the inlet port and the distal end. When the distal end of the air hose is not connected to the inflatable thermal device by way of the inlet port, the signal cannot be generated. Therefore, the presence or absence of the signal may be used to provide an indication of a connect/disconnect condition between the inlet port and the distal end of the air hose. Moreover, the information can be enriched by addition of one or more sensors at or near the junction between the inlet port and the distal end of the air hose to provide an indication of one or more air flow characteristics such as temperature or pressure, or both. It may be desirable to provide a power override function that turns off the heater/blower unit or places it in a standby condition in response either a disconnect condition indication or measurement of a temperature and/or pressure at the distal end of the air hose that deviates from a predetermined value.

Accordingly, it is an object to invest a convective warming system that includes an inflatable thermal device with the ability to sense and react to air flow conditions at a point where an air flow is provided through an inlet port of the device.

Another object is to disable, prevent, or attenuate the operation of a convective warming system when the inflatable thermal device becomes unintentionally detached from a heater/blower unit.

These and other objects and advantages of this invention will become evident when the following detailed description is read in conjunction with the below-described drawings.

DETAILED DESCRIPTION OF THE PREFERRED EMBODIMENTS

Figure 1:
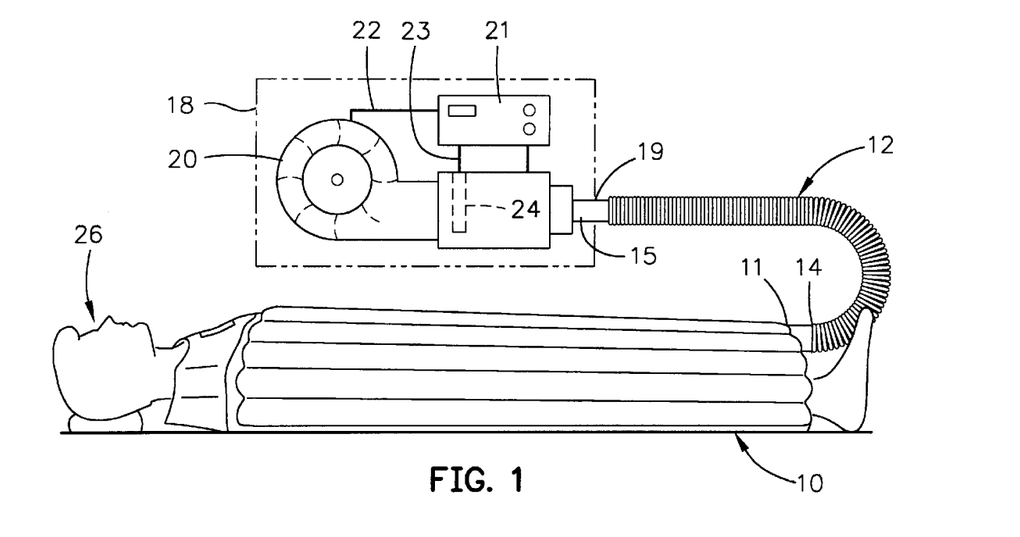
FIG. 1. Is an illustration of a convective warming system in which the invention may be embodied.

FIG. 1 illustrates a convective warming system that is operated to control the body temperature of a person by convecting thermally-regulated air from an inflatable thermal device in the direction of the person's skin. The convective warming system of FIG. 1 provides a stream of pressurized, thermally-regulated air to an inflatable thermal device through an inlet port of the device. In FIG. 1, the inflatable thermal device is an inflatable thermal blanket, of the type sold by Augustine Medical, Inc. under the BAIR HUGGER® trademark. This, however, is for purposes of illustration only. In fact, any and all equivalent inflatable thermal devices including blankets, pads, mattresses, covers, and equivalent structures are intended to enjoy the benefits of this invention.

With greater specificity, the convective warming system of FIG. 1 includes an inflatable thermal device 10 having one or more inlet ports through which a flow of pressurized, thermally-regulated air is admitted to inflate the inflatable thermal device 10. One such inlet port is indicated by reference numeral 11. In the BAIR HUGGER® family of inflatable thermal blankets, inlet ports typically comprise an opening into an inflatable structure and a stiff planar member of cardboard having an aperture. The planar member of cardboard is mounted to the inflatable structure such that the aperture in the member is aligned with the opening in the inflatable structure. The planar member is commonly referred to as a "hose card" because it provides a flat, card-like structural element that receives and supports the distal end of an air hose when the distal end is joined, mated, coupled or received in the inlet port. However, this invention is not intended to be limited to an inflatable thermal device with such inlet ports. In fact, in the inflatable thermal blanket art many inlet port structures are known and include, for example, sleeves, openings, collars, and the like. Furthermore, an inflatable thermal device may include more than one inlet port. In this regard, many models of inflatable thermal devices have two—and sometimes more—inlet ports located at various positions in order to provide flexibility in arranging the elements of a convective warming system.

In the convective warming system of FIG. 1, the inflatable thermal device 10 is inflated by a stream of pressurized, thermally-regulated (warmed) air provided through an air hose 12 having a distal (far) end 14 and proximal (near) end 15. The distal end 14 is joined, mated, coupled, or received in one of the inlet ports of the inflatable thermal device 10. In FIG. 1, the distal end 14 is received in the inlet port 11. In other words, the inlet port 11 and the distal end 14 form a junction through which an air flow is provided to inflate the inflatable thermal device 10. A heater/blower unit 18 generates and provides a flow of pressurized, thermally-regulated air (hereinafter referred to as "an airflow"). In this regard, the unit 18 includes a port 19 in which the proximal end 15 of the air hose 12 is received. Through the port 19, the proximal end 15 is coupled, mated, received in, or otherwise joined to an outlet of a blower 20. The unit 18 includes a control unit 21 with user-accessible controls that may be used to set levels or magnitudes of air flow heat and air flow velocity. A signal for air flow velocity is provided by the control unit 21 on signal path 22 where it is coupled to the blower 20 to control the speed of a blower motor (not shown) that propels air through the blower 20. The control unit 21 further generates a signal on signal path 23 that controls the operation of a heater 24 disposed near the outlet of the blower 20 for heating the air flow. Heater/blower units with user-accessible controls as just described are commercially available. Examples are the 200 and 500 series warming units available from Augustine Medical, Inc.

In the example selected for illustration of the convective warming system of FIG. 1, the inflatable thermal device 10 is placed on a person 26. This is not intended to limit the application of this invention to warming only or to use with humans. Indeed, it may be used in any system that thermally regulates persons, animals, or things using an inflatable thermal device.

Figure 2:
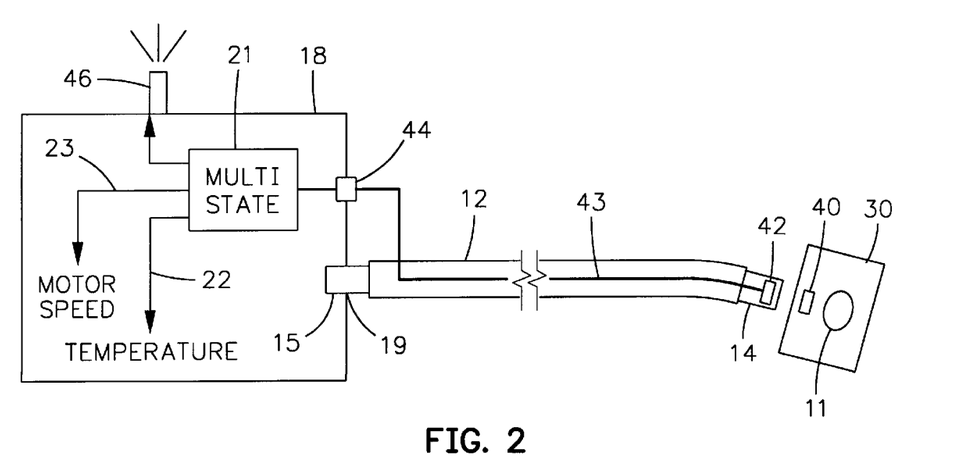
FIG. 2 is a block diagram showing the elements of the invention and their relationships to each other and to the elements of a convective warming system.

Refer now to FIG. 2 for an understanding of the invention. Although FIG. 2 includes a set of specifically-described elements, it is to be understood that wherever any such elements have structural and/or functional equivalents, such alternatives are considered to be within the scope of the invention. In FIG. 2, a convective warming system constructed and operated according to the invention includes an inflatable thermal device (not shown) having one or more inlet ports, one of which is indicated by reference numeral 11. The distal end 14 of the air hose 12 is intended to be coupled to or received in the inlet port 11; however, these elements are shown separated in FIG. 2 in order to more clearly illustrate the complement of elements that make up the invention. The proximal end 15 of the air hose 12 is received in the port 19 of the heater/blower unit 18. The invention contemplates the combination of the just-described elements with a combination of elements that operate cooperatively to detect a condition between the distal end 14 of the air hose 12 and the inlet port 11 of the inflatable thermal device. These elements include a first circuit element 40 that is disposed in, on, at or near the inlet port 11. For example, the first circuit element 40 may be formed an as integral part of a hose card 30. A second circuit element 42 is located in, on, at, or near the distal end 42 of the air hose 12, and a signal path including one or more signal conductors 43 extends in or along the air hose 12 to the proximal end 15. At or near the proximal end 15 of the air hose 12, the signal path 43 is connected at connector 44 to the control unit 21 of the heater/blower unit 18. The combination of elements 40, 42 and 43 provides a circuit for detecting a condition that may develop or exist between the distal end 14 of the air hose 12 and the inlet port 11. In other words, these elements enable the generation or conduction of a signal that represents the condition. Such a condition may be embodied, for example, in the disengagement of the distal end 14 from the inlet port 11 while the heater/blower unit 18 is operating. Another condition, for example, could include a change in the temperature of the air flow through the distal end 14 or the inlet port 11, or through the junction formed between the distal end 14 and the inlet port 11 while the heater/blower unit 18 is operating. Yet another condition may be a change in the air flow velocity through the distal end 14 or the inlet port, or through the junction formed between the distal end 14 and the inlet port 11 while the unit 18 is operating. In this latter regard, the inverse of the condition would correspond to a decrease in the air flow resistance or a decrease in the air pressure at the distal end 14 of the air hose 12 or the inlet port 11, or in the junction between the distal end 14 and the inlet port 11 while the unit 18 is operating. Whatever the condition or conditions that the invention is deployed to detect, sensing is provided by cooperative operation between the first circuit element 40 and the second circuit element 42 when the distal end 14 is joined, mated, coupled or received in the inlet port 11. In this regard, the junction formed between the distal end 14 and the inlet port 11 brings the first and second circuit elements 40 and 42 into close proximity and/or alignment. For so long as the proximity and/or alignment is maintained while the heater/blower unit 18 is operating, a first indication or signal may be generated and conducted on the signal path 43 to the control unit 21. A change in the condition is sensed by the cooperative operation of the first and second circuit elements 40 and 42, with the change in condition causing a change in the signal conducted on 43. A change in the signal conducted on 43 that is observed by the control unit 21 while the heater/blower unit 18 is operating causes the control unit 21 to take any one or more of a number of actions. First, the control unit 21 may simply cause the generation of a perceptible indication. In this regard, an indicator 46 may provide a visual and/or audible indication of a changed condition. In addition, or alternatively, the control unit 21 may respond to a change in condition by changing the motor speed of the blower 20 and/or the temperature of the warming element 24. Further, the control unit 21 may be designed or adapted to shut down or stop the operation of the heater/blower unit 18 altogether, or to place it in a standby state during which the temperature and/or velocity of the flow of air may be reduced.

The cooperative operation of the first and second circuit elements can also provide a "first necessary condition" for starting the heater/blower unit 18, preventing it from being turned on, or becoming fully operational after being turned on, in response to disconnection or non-connection of the distal end 14 and the inlet port 11 prior to operation of the heater/blower unit 18. Stated another way, the invention would permit the heater/blower unit 18 to be turned on, or to be fully operational only upon detection of joinder, coupling, or mating of the distal end 14 with the inlet port 11.

Figures 3A, 3B:
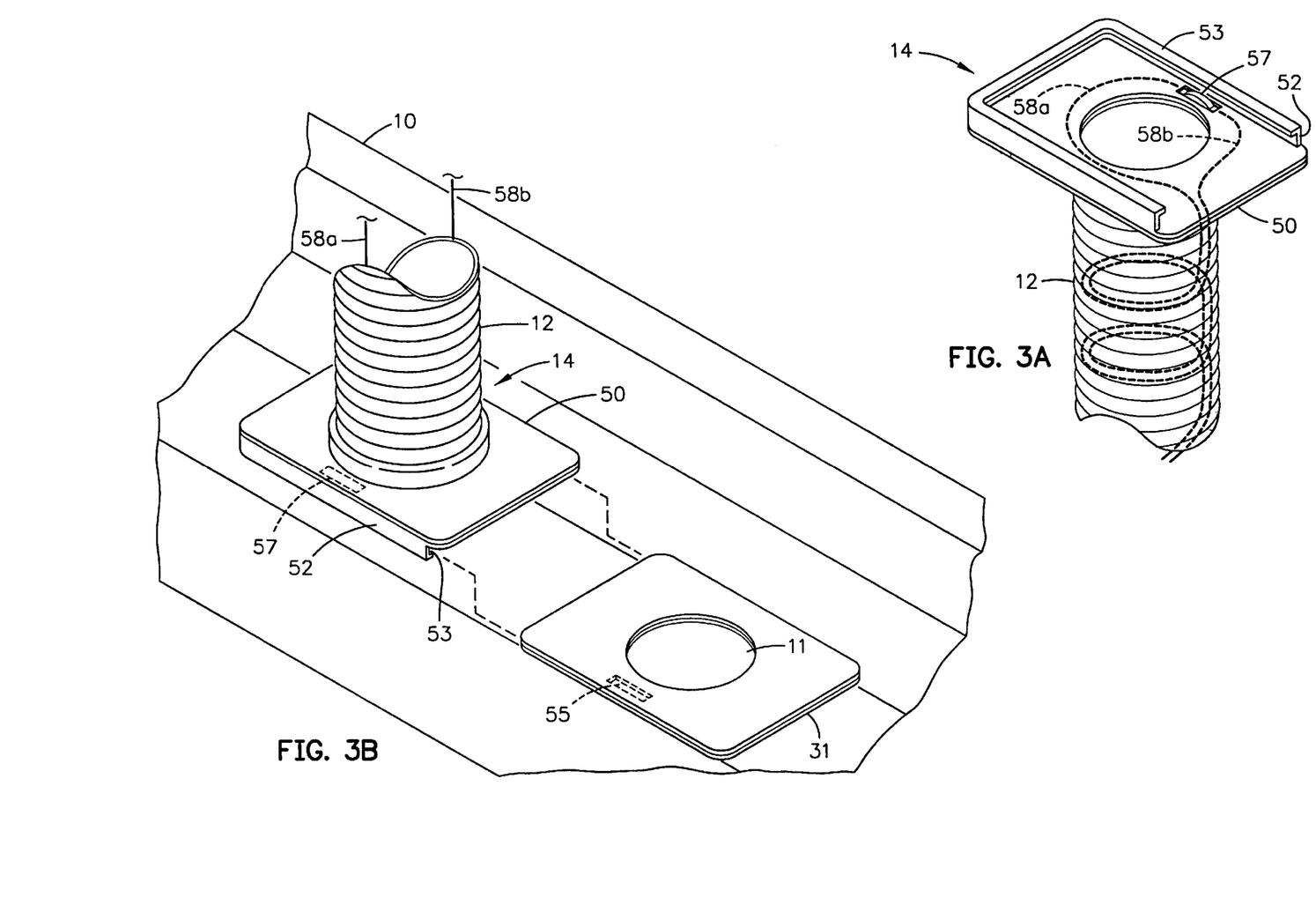
FIGS. 3A and 3B illustrate an air hose, an inflatable thermal device and elements of a presence sensor according to the invention that monitors continuity of the connection between the distal end of the air hose and an inlet port of the device.

FIGS. 3A and 3B illustrate an embodiment of the invention wherein mating of the air hose distal end with the inlet port is detected and indicated. Although these figures illustrate an inlet port of a certain construction, those skilled in the art will realize that the principles represented in these figures can be applied to other air hose/inlet port configurations. In FIGS. 3A and 3B, the hose card 30 is shown mounted on the inflatable thermal device 10 at the inlet port 11. The distal end 14 of the air hose has mounted to it a mechanism that aligns the distal end 14 with the inlet port 11 thereby to join, couple, or mate these elements, or otherwise form a junction between them. The mechanism includes a planar member 50 having generally the same shape and construction as the hose card 30 with the addition of an extending edge 52 that transitions into a lip 53. The extending edge 52 extends substantially along three sides of the periphery of the planar member 50 so that the distal end 14 can be joined, mated, coupled or received in the inlet port 11 by engaging the edges 31 of the hose card 30 between the lip 53 and a surface of the planar member 50. In FIGS. 3A and 3B, a first circuit element 55 is incorporated into the structure of the hose card 30 laterally of the opening in the hose card 30 that communicates with the inlet port 11. A second circuit element 57 is disposed in the planar member 50 laterally of the opening in the distal end 14 of the air hose 12. One or more signal conductors 58a and 58b are disposed in (or on) the air hose 12, extending from the distal end 14, along the air hose 12 toward its proximal end (not shown in these figures). Integration of signal wires into an air hose is within the ambit of modern manufacturing technology. Reference is given, for example, to vacuum cleaner hoses with embedded power conductors. In the figures, two electrical wires 58a and 58b are shown: their purpose is to conduct signals to the control unit 21. When the hose card 30 is received between the lip 53 and the planar member 50 so that the opening in the distal end 14 is aligned with the inlet port 11, the first circuit element 55 and the second circuit element 57 cooperate to complete or close a circuit between the one or more conductors 58a and 58b that is connected to the control unit 21. Many possible configurations of this circuit are possible for implementing as much of the invention as is illustrated in FIGS. 3A and 3B. For example, the first circuit element 55 may comprise a magnetic member and the second circuit element 57 may comprise a reed switch or a Hall effect device. In this case, when the first and second circuit elements 55 and 57 are placed in close proximity by mating of the distal end 14 with the inlet port 11, the magnetic member 55 causes the reed switch to close, connecting the two electrical conductors 58a and 58b, thereby creating a signal pathway along which a signal may be conducted. Conversely, when the distal end 14 is disengaged from the inlet port 11, the first and second circuit members 55 and 57 will be moved apart, causing the reed switch to open, which will disable, interrupt or open the signal path just described. This of course will prevent the conduction of a signal. Other mechanisms may be used for the first and second circuit elements 55 and 57 and for the one or more conductors 58a and 58b. For example, the first circuit element 55 may comprise a spring-loaded bar of conductive material, while the second circuit element 57 may comprise two spaced-apart terminals or posts to which the electrical conductors 58a and 58b are respectively connected. When the first and second circuit elements 55 and 57 are in close proximity, it is contemplated that the conductive bar in the hose card 30 would span and contact the posts, providing a conductive path therebetween. In yet another alternate implementation, the first circuit element 55 may comprise a spring-loaded, protruding member and the second circuit element 57 could comprise a mechanical switch that is operated by the protruding member when the distal end 14 is joined to the inlet port 11. In yet another implementation, the circuit could be an optical one in which the conductors 58a and 58b are optical fibers that terminate in optical connectors in the second circuit element 57. In this case, the first circuit element 55 could include an optical coupler that would complete an optical signal path between the ends of the two optical conductors. Alternatively, means exist for implementing an optical circuit using a single optical fiber terminated at the second circuit element 57 and a mirror incorporated in the first circuit element 55.

The first and second circuit elements 55 and 57 in FIGS. 3A and 3B operate cooperatively to provide a sensor-like function. In this regard, the sensor could be termed a "presence" sensor in that it senses the presence of the inlet port 11 from the standpoint of the distal end 14, or, conversely, it senses the presence of the distal end 14 with respect to the inlet port 11. From another point of view, the first and second circuit elements operate cooperatively as a switch with OPEN and CLOSED positions. The OPEN position would indicate separation or disconnection between the distal end 14 and the inlet port 11 or discontinuity of the junction formed between the distal end 14 and the inlet port 11. The CLOSED position, on the other hand, would indicate joining or connection of the distal end 14 with the inlet port 11, or continuity of the junction formed therebetween.

Figure 4A:
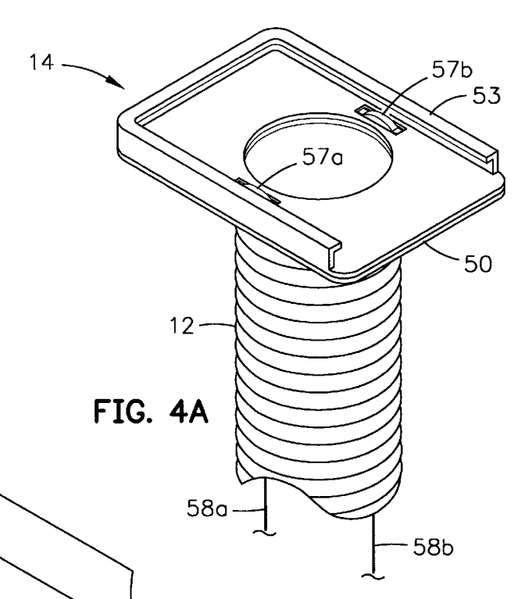
FIGS. 4A and 4B illustrate the elements of FIGS. 3A and 3B, with the addition of an airflow sensor located at the inlet port.
Figure 4B:
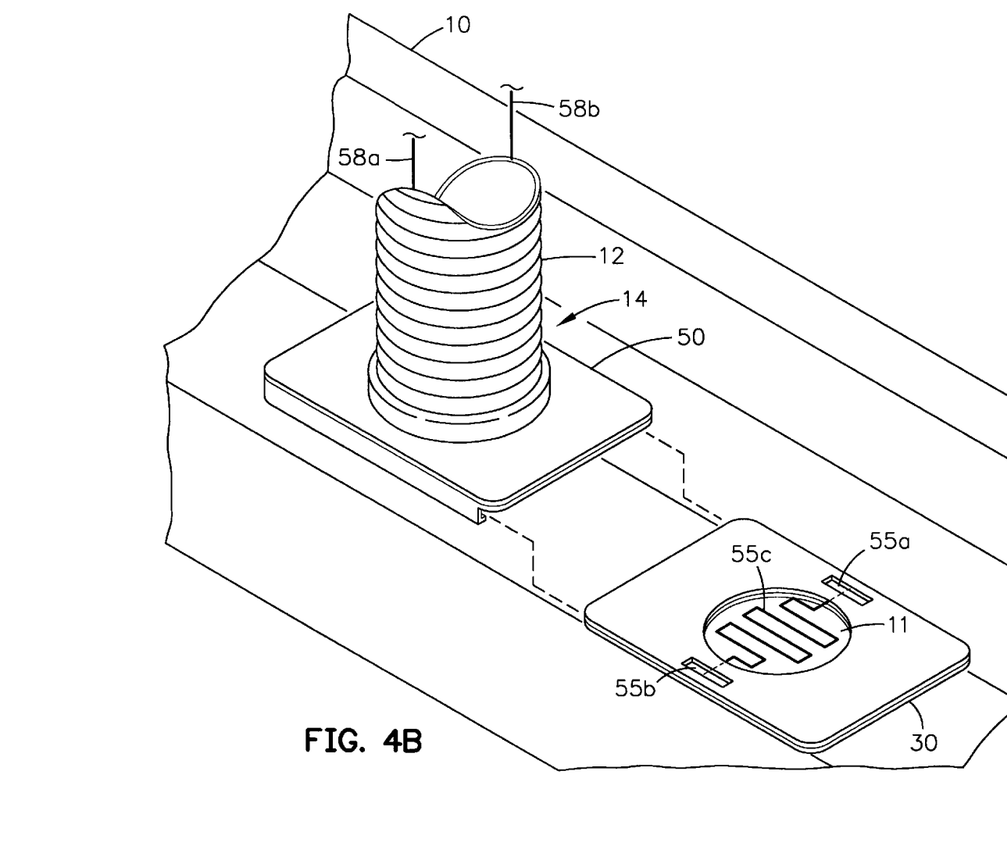

FIGS. 4A and 4B illustrate how the information provided by the simple two-state switch of FIGS. 3A and 3B can be enriched by provision of an air flow sensor at the junction formed between the distal end 14 and inlet port 11. In the description an "air flow sensor" is a sensor that detects one or more air flow conditions and causes generation of a signal having a component that reports the magnitude of the sensed conditions(s). The air flow conditions may include, for example, temperature and velocity. In FIGS. 4A and 4B, the first circuit element comprehends a first conductive contact element 55a, a second conductive contact element 55b and a sensor 55c. The first and second elements 55a and 55b are physically and electrically connected to the sensor 55c, which is disposed in the opening of the hose card 30 in alignment with the inlet port 11. Again, the elements 55a, 55b, and 55c are integrated into the structure of the hose card 30, although this is not intended to limit the implementation of a sensor at the junction between the distal end 14 and the inlet port 11. The second circuit element includes first and second conductive contact elements 57a and 57b disposed in the planar member 50 laterally of the opening in the distal end 14. When the planar member 50 fully engages the hose card 30 to join the distal end 14 with the inlet port 11, the contact element 55a mechanically and electrically contacts the contact element 57a, while the contact element 55b, physically and electrically contacts the contact element 57b. The electrical conductors 58a and 58b are connected, respectively, to the second circuit element contact elements 57a and 57b. Now, when the hose card 30 is engaged by the planar member 50, the presence sensor function will be performed by completion of an electrical signal path comprising 58a, 57a, 55a, 55c, 55b, 57b, and 58b. In addition, the sensor 55c, being disposed in the junction formed between the distal end 14 and the inlet port 11 provides the ability to sense and indicate characteristics of the air flow in the junction. In this regard, assuming that the sensor 55c comprises a thermocouple, the temperature of the air flow could be measured and reported in the form of a signal. The sensor 55c could also be configured to sense the velocity of the air flow at the same point using a hot-wire anemometer, for example. Moreover, two sensors and two circuits could be incorporated in the manner illustrated in FIGS. 4A and 4B to indicate presence, air flow temperature, and air flow velocity, or any combination thereof. Manifestly, optical elements exist which may be assembled using FIGS. 4A and 4B and the description just given to implement presence, temperature, and/or pressure sensing at the junction between the distal end 14 and inlet port 11.

Figure 5A:
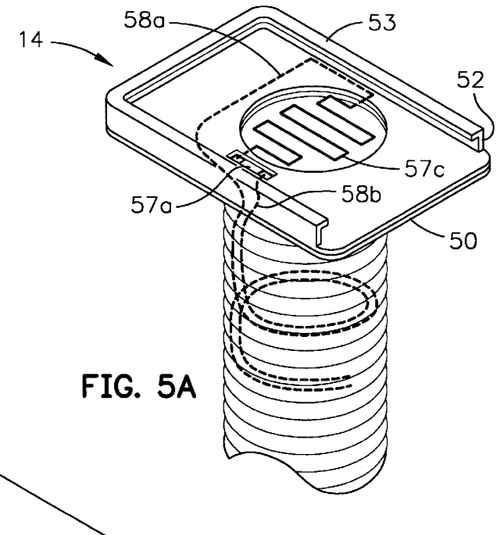
FIGS. 5A–5D, illustrate the elements of FIGS. 3A and 3B with the addition of an airflow sensor located in the distal end.
Figure 5B:
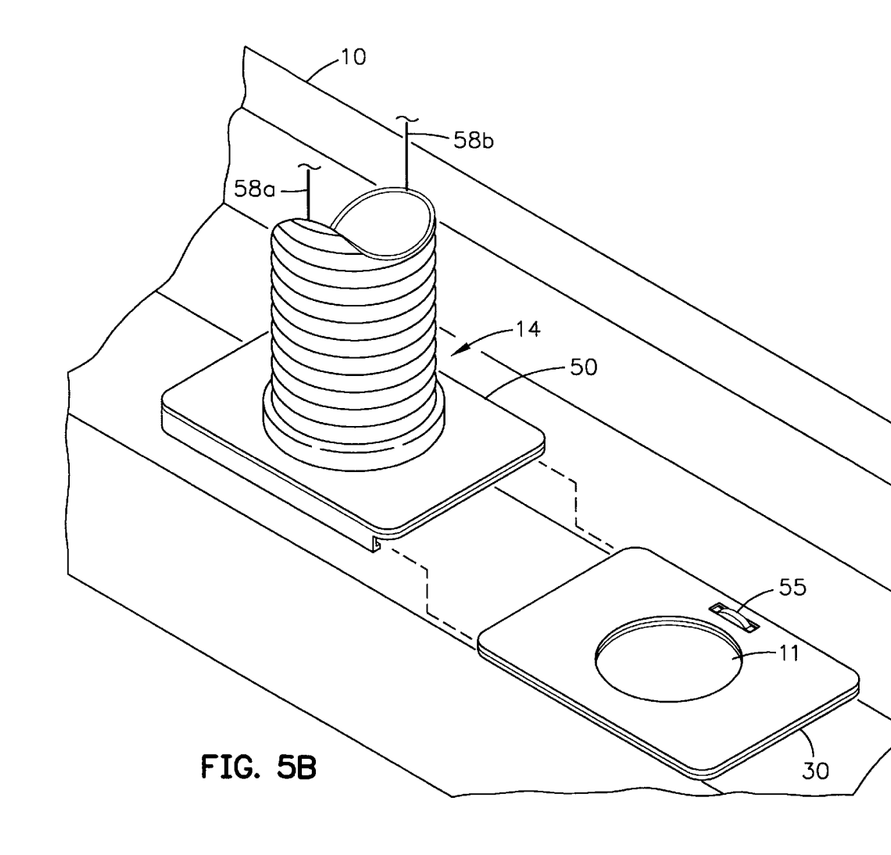

FIGS. 5A and 5B illustrate disposition of a sensor in, at, on, or near the distal end 14. In this case, the first circuit element 55 may comprise a magnetic piece, a spring-loaded activator for a mechanical switch, or spring-loaded conductive strip. At the distal end 14, the second circuit element includes a terminal element 57a and a sensor element 57c. The terminal element 57a operates cooperatively with the first circuit element 55 to complete an electrical circuit allowing the sensor 57c to operate in the junction between the distal end 14 and inlet port 11. In this case, the contact element 57a may comprise a reed switch, a hall effect device, a mechanical switch, or two conductive posts, while the sensor element 57c may comprise a thermocouple or an air velocity sensor. As with the example illustrated in FIGS. 4A and 4B, the examples of FIGS. 5A and 5B may incorporate more than one sensor at or near the distal end 14 and may sense presence, temperature and/or velocity. Furthermore, optical elements exist that could be incorporated to provide an analog of the electrical circuit shown in FIGS. 5A and 5B.

Figure 5C:
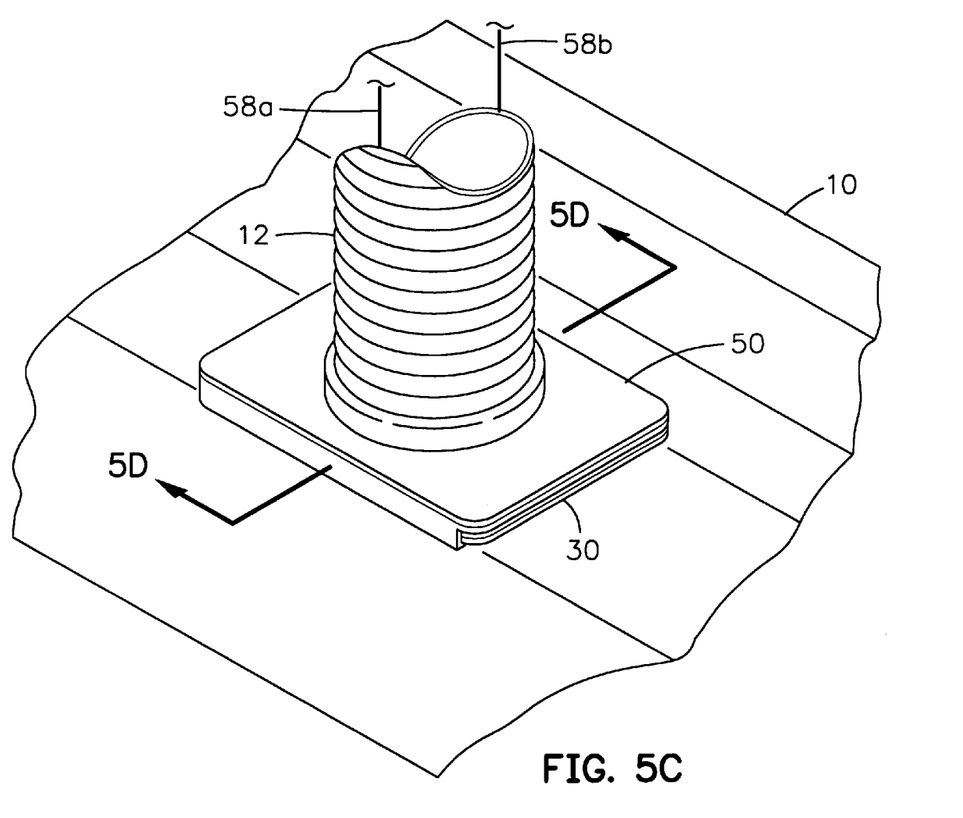
Figure 5D:
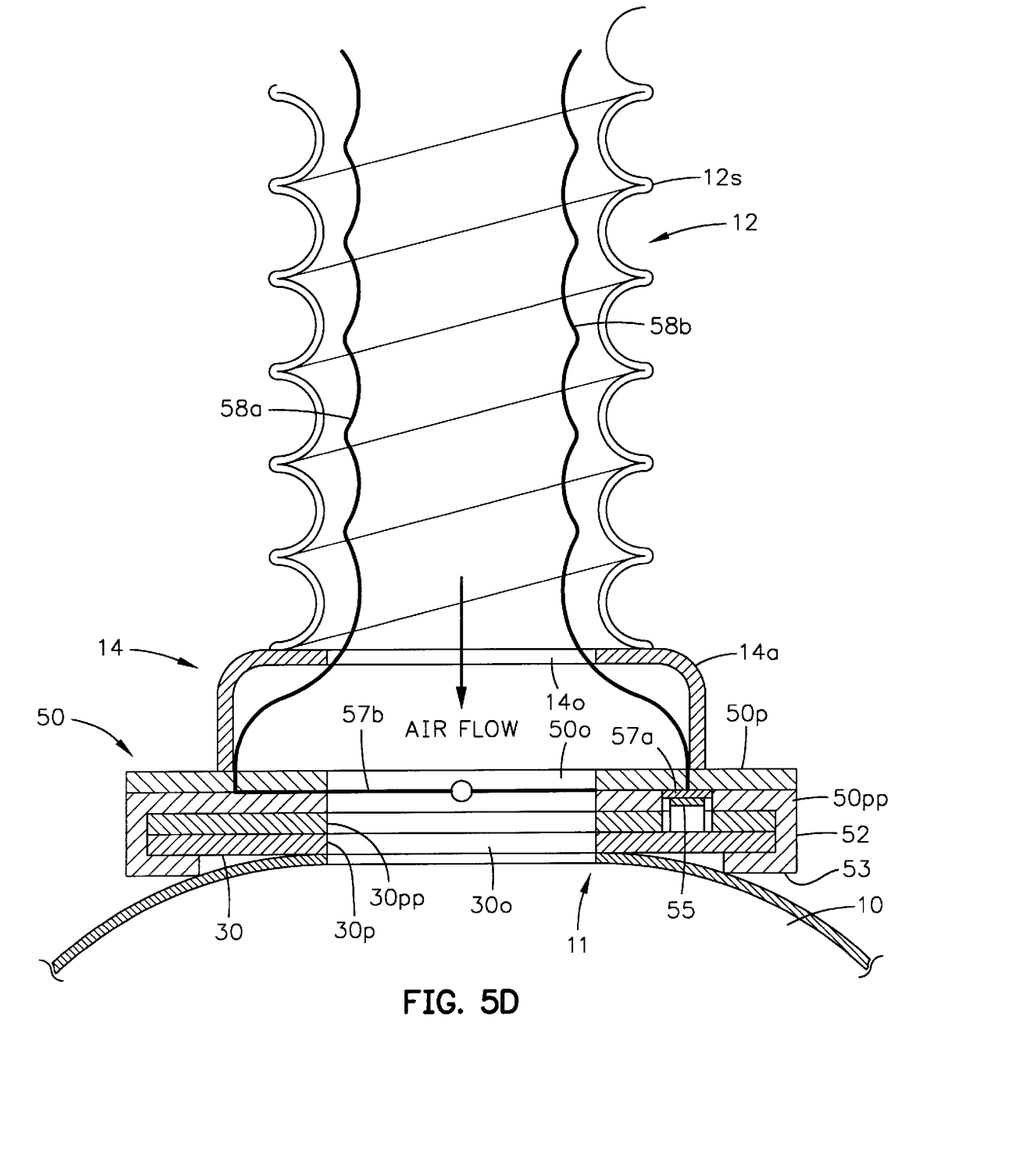

FIGS. 5C and 5D continue the illustration of the invention presented in FIGS. 5A and 5B. FIG. 5C shows the planar member 50 engaged with the hose cord 30 thereby to join, couple, or mate the distal end 14 with the inlet port 11. FIG. 5D is a side sectional elevation view taken along lines D—D in FIG. 5C. In FIG. 5D, the air hose 12, has a conventional construction that includes a flexible side wall 12s. In addition, the conductors 58a and 58b are embedded in, formed in, or attached to the side wall 12s. The air hose 12 terminates at the distal end 14 in a cup-shaped plastic member 14a having a disk-shaped opening 14o. The rim of the plastic member 14a is attached to the planar member 50. The planar member 50 includes a first plate 50p, preferably a plastic piece to which the rim of the plastic member 14a is bonded or joined. Another plastic piece 50*pp* is attached to the plastic piece 50*p*; this piece 50*pp* includes the extending side wall 52 and the lip 53. The pieces 50*p* and 50*pp* are joined or otherwise bonded together to form the planar member 50 as a single, unitary piece. The thermocouple 57*c* is held between the two pieces 50*p* and 50*pp* and includes a portion that extends across an opening 50*o* provided through the planar member 50. The hose card 30 includes two planar pieces 30*p* and 30*pp* that are glued or bonded together. An opening 30*o* in communication with the inlet port 11 aligns with the openings 50*o* and 14*o* so that an air flow path extends through the air hose 12 and the openings 14*o*, 50*o* and 30*o*. One contact 57*a* is fixed in the planar member 50 at a location where it is contacted by the shorting bar 55 when the planar member 50 is seated on the hose card 30 as shown in FIGS. 5C and 5D.

Figure 6A:
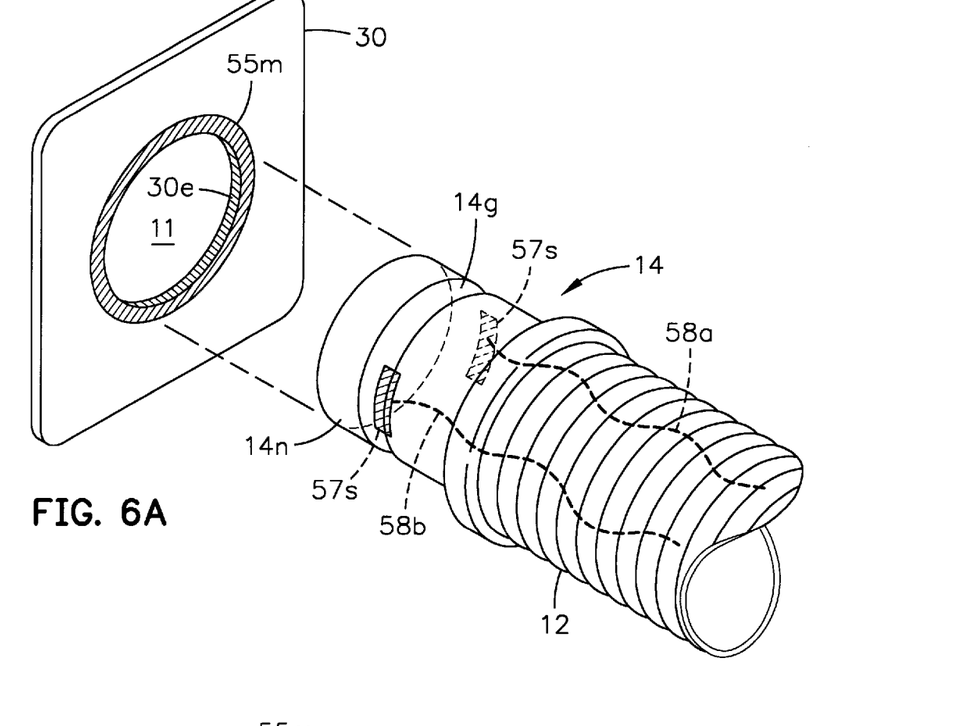
FIGS. 6A and 6B illustrate an alternate embodiment of the presence sensor of FIGS. 3A and 3B.
Figure 6B:
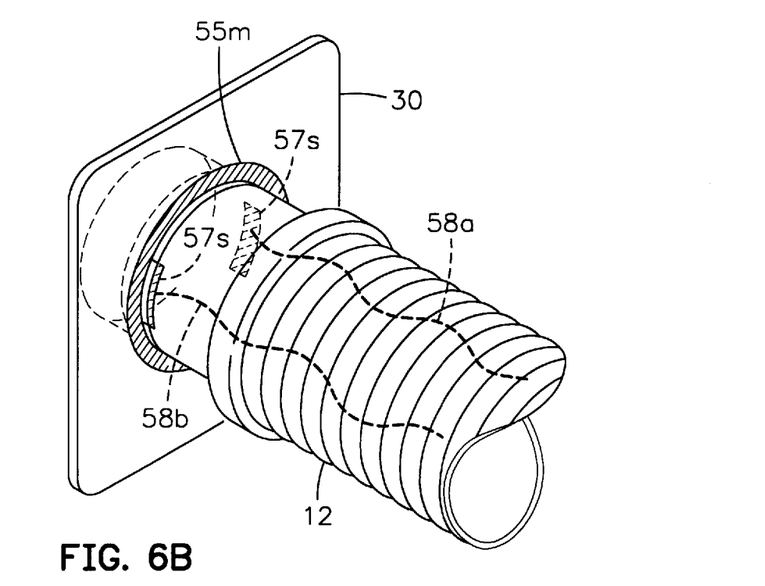

FIGS. 6A and 6B illustrate an alternative embodiment of a presence sensor in which the opening in the center of the hose card 30 includes an edge 30*e* on and adjacent to which a conductive material 55*m* is disposed. The distal end 14 of the air hose 12 is configured as a nozzle 14*n* having a circumferential groove 14*g* in which two strips of conductive material 57*s* are disposed. Each of the strips 57*s* is connected to a respective one of the conductors 58*a* and 58*b* so that when the nozzle 14*n* is inserted into the hole in the hose card 30, the groove 14*g* seats on the edge 30*c* and the material 55*m* completes or closes an electrically conductive pathway between the strips 57*s*.

Figure 7:
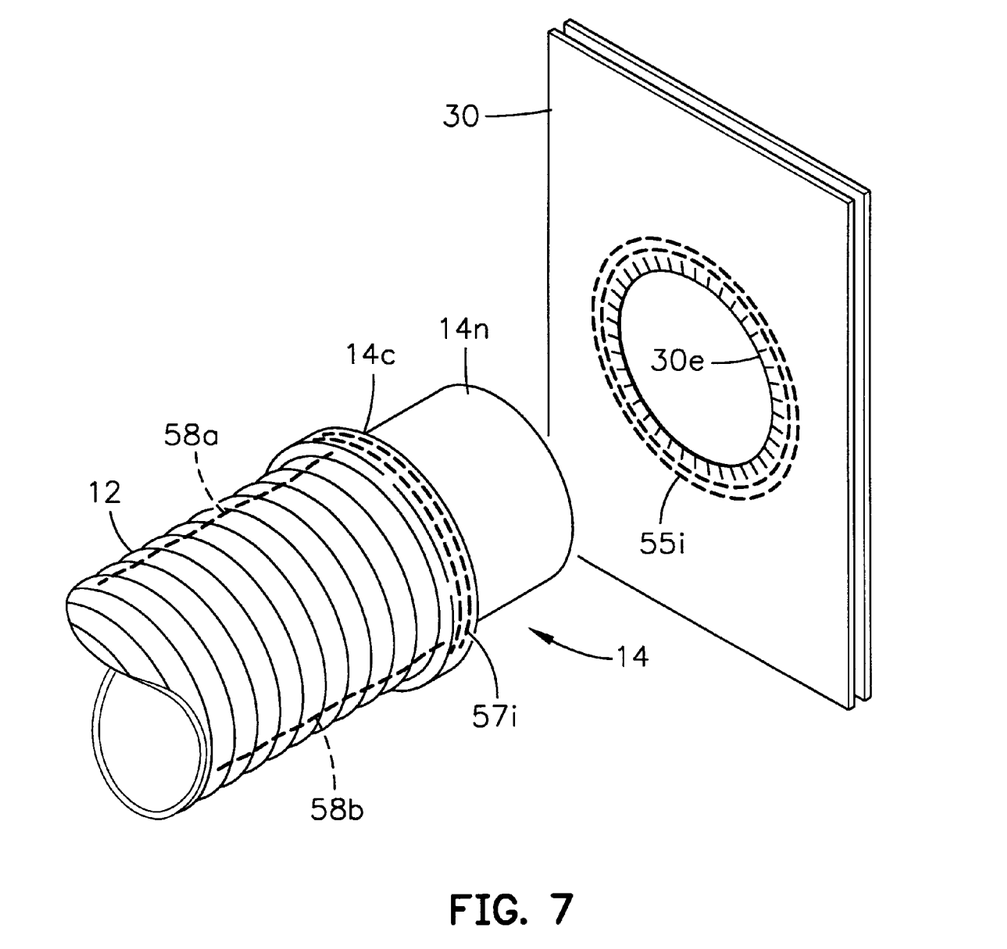
FIG. 7 illustrates another alternate embodiment of the presence sensor of FIGS. 3A and 3B.

Yet another implementation of the presence sensor is illustrated in FIG. 7 wherein the distal end 14 of the air hose 12 includes the nozzle 14*n* which transitions to a collar 14*c* within which a coil 57*i* is embedded. The coil 57*i* is connected to and driven by the conductors 58*a* and 58*b*. Disconnected from the hose card 30, the coil 57*i* exhibits an impedance having an electromagnetic characteristic (impedence, with an inductive component). A second coil 55*i* is embedded in the hose card 30*e* around the edge 30*e*. Now, when the distal end 14 of the air hose 12 is seated in the hose card so that the collar 14*c* is adjacent the edge 30*e*, the impedance driven by the conductors 58*a* and 58*b* has a value measurably different from that exhibited by the coil 57*i* when the distal end 14 is not seated in the hose card 30. Alternatively, the coils 57*i* and 55*i* could be replaced with insulated conductive elements that exhibit a measurable capacitance whose value changes when the distal end 14 and the inlet port 11 are connected and disconnected.

One way in which to measure a change in an electromagnetic characteristic at the junction between the distal end 14 and the inlet port 11 would be to drive the circuit 58*a*, 57*i*, 58*b* with a signal of known frequency generated by the control unit 21. A change in the characteristic would be manifested by a change in frequency of the signal.

Figure 8A:
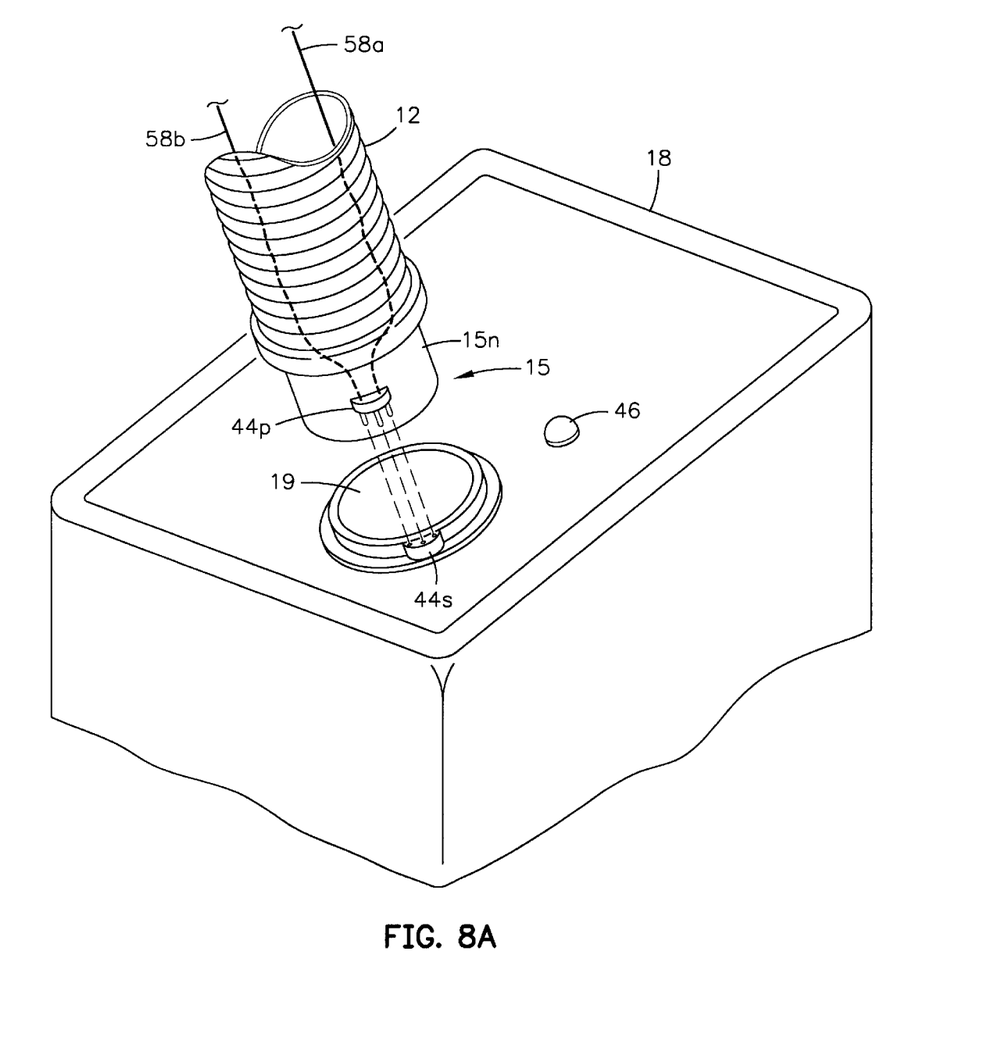
FIGS. 8A and 8B illustrate how the proximal end of the air hose may be coupled to a heater/blower unit according to the invention.
Figure 8B:
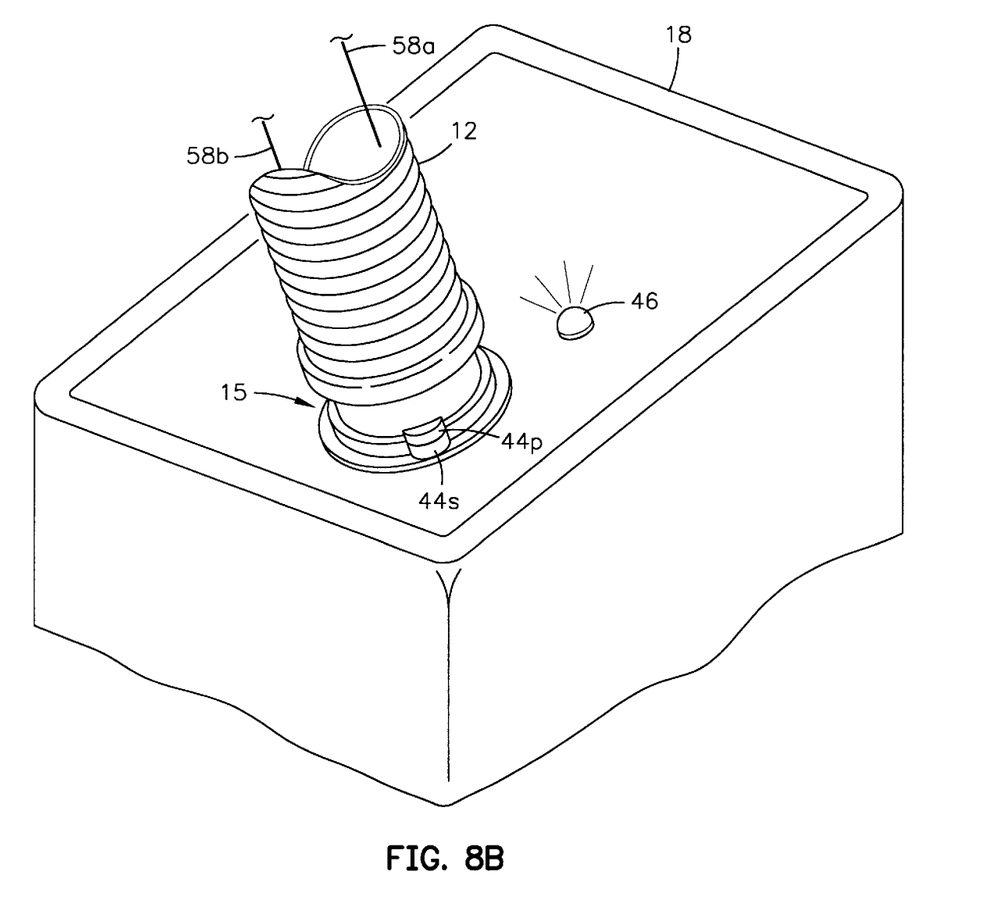

FIGS. 8A and 8B illustrate how a connection is made to the heater/blower unit 18 at the proximal end of 15 of the air hose 12, to provide continuity of a signal pathway to the control unit 21 (not shown). In this regard, a connector plug 44*p* is mounted on a proximal end nozzle 15*n*. The conductors 58*a* and 58*b* terminate on respective pins of the plug 44*p*. When the nozzle 15*n* is received in the port 19 of the unit 18, the pins of the plug 44*p* are received in respective receptacles of a connector socket 44*s* mounted on the unit 18, adjacent to the port 19, in alignment with the pins of the plug 14*p*. As shown in FIG. 8B, when the plug 44*p* and socket 44*s* are mated, the indicator 46 provides (in this example) a visual indication of joinder, mating, coupling, or connection between the distal end 14 of the air hose 12 and one of one or more inlet ports of an inflatable thermal device.

Figure 9:
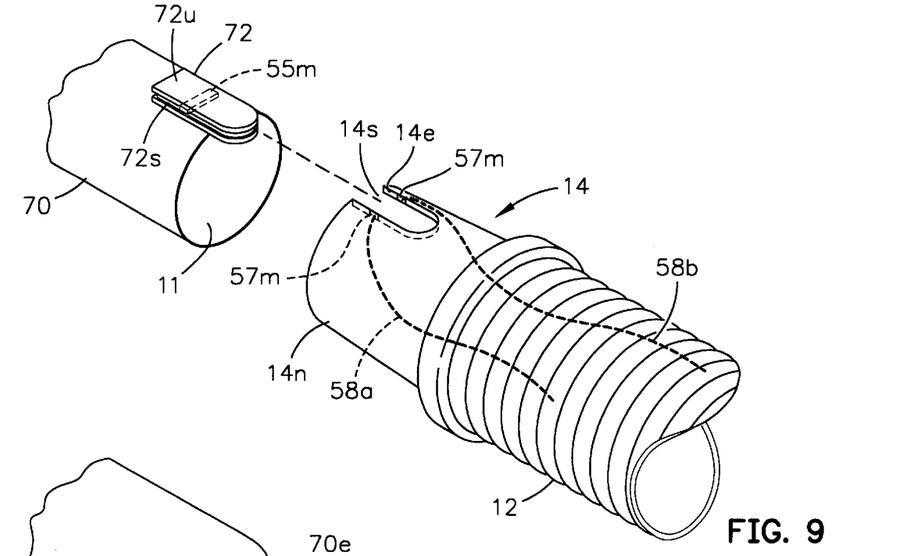
FIG. 9 shows a presence sensor in an inflatable thermal device in which an inlet port is provided as a sleeve.
Figure 10A:
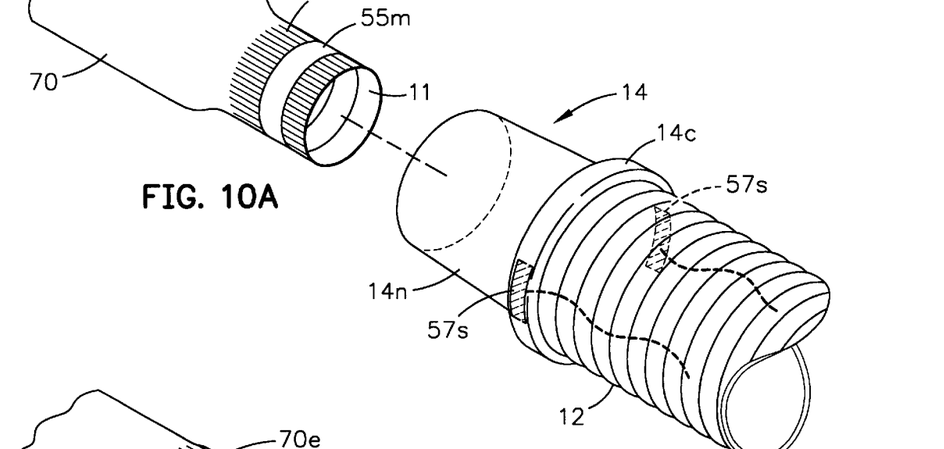
FIGS. 10A and 10B show an alternate embodiment of the presence detector of FIG. 9.
Figure 10B:
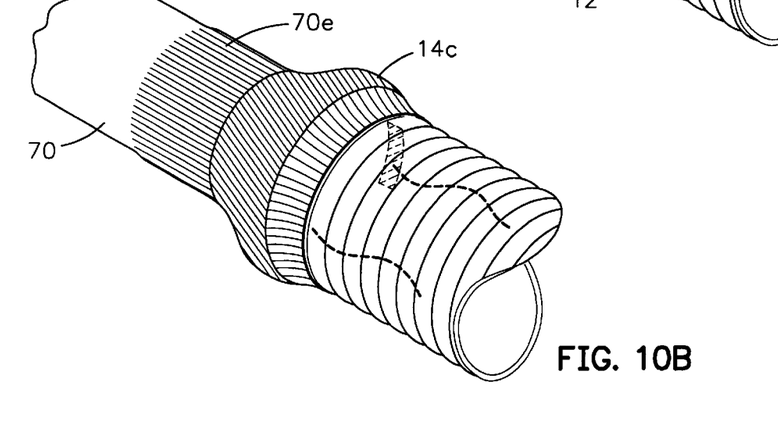

FIGS. 9, 10A and 10B illustrate how the invention may be adapted to inlet ports having sleeve-like constructions. Referring to FIG. 9, the distal end 14 of the air hose 12 has the nozzle 14*n* in which a slot 14*s* is cut. An edge 14*e* of the slot is exposed and elements of conductive material 57*m* are placed on the edge 14*e*, in opposition across the slot 14*s*. The inlet port 11 is embodied in a sleeve 70 of material that extends from and opens into an inflatable thermal device (not shown). An alignment and contact mechanism 72 is mounted on the inside of the sleeve 70 by appropriate means including, for example, glueing between the inside surface of the sleeve and the upper surface 72*u* of the alignment mechanism 72. The alignment mechanism 72 may be a molded plastic piece that generally has the shape of the slot 14*s* and includes a peripheral slot-like recess 72*s* that receives the edge 14*e* of the slot 14*s*. A strip of conductive material 55*m* is disposed in the alignment mechanism 72, protruding in the opposed places into the peripheral slot-like recess 72*s*. When the slot 14*s* is seated on the alignment mechanism 72, an electrical circuit is completed or closed between the conductive material elements 57*m* by way of the strip of conductive material 55*m*. In FIGS. 10A and 10B, the end of the sleeve 70 has an elastic material integrated into the material of the sleeve 70 to form an elastic portion 70*e*. On the inside surface of the elastic portion 70*e* a ring of conductive material 55*m* is attached. The distal end 14 of the air hose 12 has substantially the same construction as that illustrated in FIGS. 6A and 6B, with the exception that the circumferential groove 14*g* is omitted. To join, couple, the distal end 14 in the inlet port 11 via the sleeve 70, the elastic region 70*e* is expanded, and the distal end 14 is slid into the sleeve 70 until the collar 14*c* is in the portion of the elastic region 70*e* that is girded on its inside surface by the ring of conductive material 55*m*, which closes or otherwise completes an electrical pathway between the conductive elements 57*s*. The nozzle 14*n* is retained in the sleeve 70 by the grip of the elastic region 70*e* on the nozzle's outside surface.

Clearly, other embodiments and modifications of the present invention will occur readily to those of ordinary skill in the art in view of these teachings. For example, in inflatable thermal devices with more than one inlet port, one, some, or all of the inlet ports may have first circuit elements as illustrated in the figures. Also, a heater/blower unit with more than one air hose may fall within the scope of this invention. Further, the invention may be applied to convective systems having the elements of FIG. 1 that cool persons, animals, or things. Therefore, this invention is to be limited only by the following claims, which include all such embodiments and modifications.

We claim:

1. In a system for convectively controlling a temperature with an inflatable thermal device, a combination for monitoring a condition between an air hose and an inlet port in the inflatable thermal device, comprising:

a first circuit element at an inlet port of an inflatable thermal device; and a second circuit element near a first end of an air hose receivable in the inlet port, the second circuit element cooperating with the first circuit element to enable a signal representing a condition between the first end of the air hose and the inlet port.

2. The combination of claim 1, further including:

an indicator connected to the second circuit element for giving an indication of the condition.

3. The combination of claim 2, wherein the indication is of receipt of the first end of the air hose in the inlet port.

4. The combination of claim 2, wherein the indication is of an air stream characteristic.

5. The combination of claim 1, further including an alignment mechanism for acting between the inlet port and the first end of the air hose to register the first circuit element and the second circuit element in a predetermined alignment.

6. The combination of claim 1, wherein the first circuit element includes a sensor.

7. The combination of claim 6, wherein the first circuit element further includes at least one reed switch connected to the sensor and the second circuit element includes a mechanism for activating the reed switch.

8. The combination of claim 6, wherein the first circuit element further includes a mechanical switch connected to the sensor and the second circuit element includes a mechanism for operating the mechanical switch.

9. The combination of claim 1, wherein the first circuit element and the second circuit element act as a switch.

10. The combination of claim 1, wherein the first circuit element includes a switch and the second circuit element includes a mechanism for operating the switch.

11. The combination of claim 1, wherein the second circuit element includes a switch and the first circuit element includes a mechanism for operating the switch.

12. The combination of claim 1, further including one or more signal conductors connected to the second circuit element for being disposed in the air hose.

13. The combination of claim 12, further including an electrical plug connected to the one or more signal conductors for being positioned near a second end of the air hose.

14. The combination of claim 1, wherein the second circuit element includes a sensor.

15. The combination of claim 14, wherein the second circuit element further includes at least one reed switch connected to the sensor and the first circuit element includes a mechanism for operating the reed switch.

16. The combination of claim 14, wherein the second circuit element further includes a mechanical switch connected to the sensor and the first circuit element includes a mechanism for operating the mechanical switch.

17. An inflatable thermal device system, comprising:
an inflatable thermal device with at least one inlet port and at least one surface adapted to expel air;
an air hose with a first end and a second end;
a first circuit element at the inlet port;
a second circuit element near the first end of the air hose, the second circuit element cooperative with the first circuit element to enable a signal having a first value when the first end of the air hose is not mated with the inlet port and having a second value when the first end of the air hose is mated with the inlet port; and
one or more conductors in the air hose connected to the second circuit element for conducting the signal from the first to the second end.

18. The system of claim 17, further including an alignment mechanism acting between the inlet port and the first end of the air hose for registering the inlet port and the first end of the air hose in a predetermined alignment, the predetermined alignment placing the first and second circuit elements in close proximity.

19. The system of claim 17, wherein the first and second values are values of at least one air flow characteristic near the first end of the air hose.

20. The system of claim 17, wherein the first circuit element includes a sensor.

21. The system of claim 20, wherein the first circuit element further includes at least one reed switch connected to the sensor and the second circuit element includes a mechanism for activating the reed switch.

22. The system of claim 20, wherein the first circuit element further includes a mechanical switch connected to the sensor and the second circuit element further includes a mechanism for operating the mechanical switch.

23. The system of claim 17, wherein the second circuit element includes a sensor.

24. The system of claim 23, wherein the second circuit element further includes at least one reed switch connected to the sensor and the first circuit element includes a mechanism for operating the reed switch.

25. The system of claim 23, wherein the second circuit element further includes a mechanical switch connected to the sensor and the first circuit element includes a mechanism for operating the mechanical switch.

26. The system of claim 17, wherein the first value is indicative of receipt of the first end in the inlet port and the second value is indicative of separation of the first end from the inlet port.

27. The system of claim 17, wherein the at least one inlet port includes a hose card, the first circuit element being in the hose card.

28. The system of claim 17, wherein the at least one inlet port includes a sleeve, the first circuit element being in the sleeve.

29. The system of claim 17, further including a plug near the second end of the air hose connected to the one or more conductors and a unit for providing a flow of pressurized air, the unit including a receptacle for receiving the second end of the air hose and a receptacle for receiving the plug.

30. An inflatable thermal device, comprising:
an inflatable portion adapted to be inflated with pressurized air and to expel pressurized air;
at least one inlet port for receiving a flow of pressurized air; and
a circuit element at the at least one inlet port for causing generation of a safety indication.

31. The inflatable thermal device of claim 30, wherein the circuit element includes a thermal sensor.

32. The inflatable thermal device of claim 30, wherein the circuit element includes at least one reed switch.

33. The inflatable thermal device of claim 30, wherein the circuit element includes at least one mechanical switch.

34. The inflatable thermal device of claim 30, wherein the circuit element includes a sensor.

35. The inflatable thermal device of claim 34, wherein the sensor is an air flow temperature sensor.

36. The inflatable thermal device of claim 34, wherein the sensor is an air flow pressure sensor.

37. The inflatable thermal device of claim 34, wherein the sensor is a presence sensor.

38. An air blower unit for delivering a flow of pressurized, thermally-regulated air to an inflatable thermal device through an air hose, comprising:
an element for receiving a safety signal from a near end of the air hose; and
a control unit connected to the element for providing a first indication representing a first condition at a far end of the air hose in response to a first signal from the element and a second indication representing a second condition at the far end of the air hose in response to a second signal from the element.

39. The air blower unit of claim 38, wherein the first condition occurs when the far end of the air hose is coupled to an inlet port of an inflatable thermal device and the second condition occurs when the far end of the air hose is not connected to an inlet port of the inflatable thermal device.

40. The air blower unit of claim 38, wherein the first condition corresponds to a first temperature of pressurized air exhausted through the far end of the air hose and the second condition corresponds to a second temperature of pressurized air exhausted through the far end of the air hose.

41. The air blower unit of claim 38, wherein the element is an electrical plug.

42. A method for indicating a condition in a system including an inflatable thermal device with one or more inlet ports and at least one surface adapted to expel air, and an air hose with two ends for delivering a flow of pressurized air to the inflatable thermal device when one end is coupled with an inlet port, comprising:

coupling an end of the air hose to an inlet port of the inflatable thermal device;

operating the inflatable thermal device by conducting a flow of pressurized air through the air hose;

sensing at the inlet port a condition between the inlet port and the end of the air hose; and responding to the sensed condition.

43. The method of claim 42, wherein the condition is a connect/disconnect condition.

44. The method of claim 42, wherein the condition is an air flow condition.

45. The method of claim 42, wherein responding comprises providing an indication of the sensed condition.

46. The method of claim 42, wherein responding comprises stopping the flow of pressurized air.

47. The method of claim 42, wherein responding comprises changing an air flow characteristic of the flow of pressurized air.

48. A method for indicating a condition in a system including an inflatable thermal device with one or more inlet ports and at least one surface adapted to expel air, and an air hose with two ends for delivering a flow of pressurized air to the inflatable thermal device when one end is coupled with an inlet port, comprising:

coupling an end of the air hose to an inlet port of the inflatable thermal device;

operating the inflatable thermal device by conducting a flow of pressurized air through the air hose;

sensing at the end of the air hose a condition between the inlet port and the end of the air hose; and responding to the sensed condition.

49. The method of claim 48, wherein the condition is a connect/disconnect condition.

50. The method of claim 48, wherein the condition is an air flow condition.

51. The method of claim 48, wherein responding comprises providing an indication of the sensed condition.

52. The method of claim 48, wherein responding comprises stopping the flow of pressurized air.

53. The method of claim 48, wherein responding comprises changing an air flow characteristic of the flow of pressurized air.

54. A method for indicating a condition in a system including an inflatable thermal device with one or more inlet ports and at least one surface adapted to expel air, and an air hose with two ends for delivering a flow of pressurized air to the inflatable thermal device when one end is coupled with an inlet port, comprising:

forming a junction between an end of the air hose and an inlet port of the inflatable thermal device;

operating the inflatable thermal device by conducting a flow of pressurized air through the air hose;

sensing at the junction a condition between the end of the air hose and the inlet port; and providing an indication of the sensed condition.

55. The method of claim 54, wherein the condition is a connect/disconnect condition.

56. The method of claim 54, wherein the condition is an air flow condition.

57. The method of claim 54, wherein responding comprises providing an indication of the sensed condition.

58. The method of claim 54, wherein responding comprises stopping the flow of pressurized air.

59. The method of claim 54, wherein responding comprises changing an air flow characteristic of the flow of pressurized air.

60. A device for an inlet port of an inflatable thermal device, comprising:

a structure adapted to be received on the inlet port to retain an air hose; and a circuit element on the structure.

61. The device of claim 60, wherein the structure is a hose card.

62. The device of claim 60, wherein the circuit element includes a sensor.

63. The device of claim 62 wherein the circuit element further includes at least one switch connected to the sensor.

64. The device of claim 63, wherein the at least one switch is a reed switch.

65. The device of claim 63, wherein the at least one switch is a mechanical switch.

66. The device of claim 60, wherein the circuit element includes a mechanism for operating a switch.

67. The device of claim 62, wherein the structure is a hose card.

68. The device of claim 62, wherein the sensor is an airflow temperature sensor.

69. The device of claim 62, wherein the sensor is an airflow pressure sensor.

70. The device of claim 62, wherein the sensor is a presence sensor.

* * * * *